United States Patent [19]

Inacu et al.

[11] Patent Number: 5,918,291

[45] Date of Patent: Jun. 29, 1999

[54] METHOD FOR LIQUID ASPIRATION FROM A SEALED CONTAINER

[76] Inventors: Fulga Inacu, 91 Lake St., Pleasantville, N.Y. 10570; Spencer M. Lovette, 31 Lalli Dr., Katonah, N.Y. 10536; William McCandless, 24 Weir Place, Ringwood, N.J. 07456

[21] Appl. No.: 08/481,881

[22] Filed: Jun. 7, 1995

[51] Int. Cl.$^6$ ........................................ B01L 3/02
[52] U.S. Cl. .................... 73/863.83; 73/863.32; 73/863.81; 73/864.01
[58] Field of Search ............ 73/863.32, 863.81, 73/863.83, 863.84, 864.01

[56] References Cited

U.S. PATENT DOCUMENTS

| | | | |
|---|---|---|---|
| 3,940,995 | 3/1976 | Harris, Sr. et al. ................. | 73/422 GC |
| 4,457,184 | 7/1984 | Shiono ................................. | 73/864.11 |
| 4,951,512 | 8/1990 | Mazza et al. ....................... | 73/861.23 |
| 5,254,313 | 10/1993 | Kuroda et al. ...................... | 73/863.84 |
| 5,322,192 | 6/1994 | Godolphin et al. ................. | 222/83 |
| 5,325,861 | 7/1994 | Goulding ............................ | 73/863.83 |
| 5,341,691 | 8/1994 | Callis et al. ........................ | 73/863.83 |
| 5,348,606 | 9/1994 | Hanaway et al. ................... | 73/863.32 |
| 5,413,246 | 5/1995 | Godolphin et al. ................. | 222/1 |

FOREIGN PATENT DOCUMENTS

| | | |
|---|---|---|
| 0 452 892 | 10/1991 | European Pat. Off. . |
| WO 91/19181 | 12/1991 | WIPO . |
| WO 92/08988 | 5/1992 | WIPO . |

OTHER PUBLICATIONS

William R. Seebaugh, et al., "An Automated Device for Aseptically Aspirating Serum from Blood Collection Tubes", *IEEE Transactions on Biomedical Engineering*, vol. BME–33, No. 6, Jun. 1986, pp. 610–616.

*Primary Examiner*—George Dombroske
*Attorney, Agent, or Firm*—Wolf, Greenfield & Sacks, P.C.

[57] ABSTRACT

A method for aspirating a fluid from a sealed container and for dispensing a precise quantity of the aspirated fluid. The method involves standard steps of inserting a probe into the container through the container seal and aspirating bubbles and the selected quantity of fluid into the probe before removing the probe from the container and dispensing the fluid. The method also includes an additional step performed at at least one stage in the method to assure that, before the dispensing operation is performed, sample fluid in the probe extends to the end of the probe without any fluid extending beyond the end of the probe.

9 Claims, 2 Drawing Sheets

METHOD FOR LIQUID ASPIRATION FROM A SEALED CONTAINER

FIELD OF THE INVENTION

This invention relates to systems for aspirating and dispensing fluid from sealed containers and more particularly to a method for providing enhanced accuracy in performing such aspiration and dispensing operation.

BACKGROUND OF THE INVENTION

While the aspiration of fluids from sealed containers may be required in various industrial and laboratory settings, such procedures are most frequently performed in medical laboratories and other medical settings where blood, other bodily fluids or some reactant or dilutant is aspirated from a sealed test tube, bottle, vial or other container and is then dispensed into a cuvette or other vessel to have appropriate test procedures performed thereon. The containers in which the fluid is initially stored are frequently at a significant initial negative pressure as to both facilitate the drawing of blood into the container and to also inhibit the escape of blood from the container. However, even where the container is not negatively pressurized, the pressure in the container may vary significantly as a result of factors such as changes in the volume of fluid in the container, changes in the temperature of the fluid and on ambient temperature, and leakage through the seals. Where the blood in the container is taken directly from an individual, the pressure may also vary depending on the blood pressure of the individual from whom the blood was obtained.

Therefore, the pressure in the container at any given time can vary significantly, either positively or negatively, but generally negatively, from the ambient or atmospheric pressure outside the container. This pressure variation can cause errors in the quantity of fluid dispensed when standard fluid aspirating and dispensing procedures are utilized. In particular, the standard procedure for aspiration is to insert the probe into the container, aspirate a small gas bubble into the probe to separate the fluid being aspirated from the water or other fluid being acted on by the pump in the system, aspirate at least one small separator sample of fluid, aspirate another separator air bubble(s) and then aspirate the sample. The probe is them removed from the container and the pump of the system is operated to dispense a precise quantity of the sample.

However, if the pressure in the container is less than that outside the container, the air bubbles in the probe will shrink slightly when the probe is removed from the container, resulting in a small air gap at the tip of the probe. Therefore, when the pump attempts to dispense a precise quantity of fluid, the initial dispensing will be of air, resulting in a slight underdispensing of the blood or other fluid. Depending on the pressure differential, the size of the bubbles and the size of the sample, this underprovision of sample may be 10% or more of the desired sample and could lead to inaccurate results in medical tests being performed. Similarly, if the pressure in the container is greater than the external ambient pressure, the bubbles will expand when the probe is removed from the container, causing a drop of fluid to form at the end of the probe which can result in an over dispensing of liquid with similar undesirable results.

In the past, to the extent these problems have dealt with, they have been dealt with by assuring that the pressure in the container is equalized with the external pressure when the probe is inserted in the container, while the sample is aspirated and when the probe is removed. One way of accomplishing this objective is for example taught in U.S. Pat. No. 4,951,512 which utilizes a cannula surrounding the probe which is inserted through the seal with the probe or prior to insertion of the probe and remains in place through the aspirating operation. Air flowing through the space between the probe and cannula keeps the pressure equalized between the inside and outside of the container. While this mechanism solves the problems indicated above, it also has a number of limitations. First, when the open cannula is initially inserted into the container, blood can shoot out through cannula. With today's AIDS consciousness, any procedure which results in blood splattering or aerosol is undesirable. Second, the device is relatively complex to make and use and is much more complicated to clean than if only a probe were utilized. Finally, the cannula makes a much larger hole in the seal than would be made by the probe alone, therefore requiring a greater force to penetrate and increasing the chances an incomplete resealing of the container after the probe and cannula are removed.

It would therefore be desirable if the problem of inaccurate fluid dispensing resulting from pressure differentials between the inside and outside of the sealed container could be eliminated without the use of an additional cannula around the probe to provide continuous pressure equalization.

SUMMARY OF THE INVENTION

In accordance with the above, this invention provides a method for aspirating a fluid from a sealed container and for dispensing a precise quantity of the aspirated fluid. The method involves inserting a probe into the container through the container seal, this step being performed while maintaining the container in the sealed condition. At least one bubble is provided in the probe to separate any sample from other fluid in the probe. A selected quantity of fluid is then aspirated into the probe and the probe is removed from the container. A precise quantity of fluid is then dispensed from the probe. Finally, the operation includes the performing of at least one step at selected stages in the method to assure that, before the dispensing operation is performed, sample fluid in probe extends to the end of the probe without any fluid extending beyond the end of the probe.

For one embodiment of the invention, the fluid aspirated includes both the selected quantity of fluid to be dispensed and a selected extra volume of fluid; and the last step in the operation includes the step, performed prior to the dispensing step, of wasting a selected quantity of the sample which is greater than the maximum amount that the at least one air bubble might shrink as a result of the pressure in the container being less than the pressure outside the container, but less than the selected extra volume of fluid. This wasting step assures that, when dispensing is performed, the fluid sample will extend to the end of the probe, but that a fluid droplet will not extend beyond the end of the probe, so that the measured quantity of fluid being dispensed results in the selected quantity of fluid actually being dispensed.

To reduce the amount of fluid that needs to be wasted in the above operation where the pressure in the container is unknown, two additional steps may be performed. In particular, before the probe is inserted in the container, a volume of fluid may be withdrawn from the probe, which volume is substantially equal to least the sum of the volumes of the selected quantity of fluid to be aspirated, the at least one air bubble and the selected extra volume of fluid, the volume of fluid being withdrawn from the probe being replaced by air entering the probe. After the probe is inserted in the container, a volume of air is dispensed from the probe into the container which is substantially equal to the volume of fluid previously withdrawn, less the volume of at least one of the separator air bubbles.

For an alternative embodiment of the invention, the pressure inside and outside the container is equalized, for example by inserting a hollow needle into the container through the seal and then removing the needle before the probe is inserted. Also before the probe is inserted, a volume of fluid is withdrawn from the probe which is equal to at least the sum of the volume of the selected quantity of fluid to be aspirated and the at least one air bubble, with this withdrawn volume again being replaced by air. The pressure in the container is then increased when the probe has been inserted by dispensing the volume of air previously drawn into the probe, less the volume of at least one of the air bubbles, into the container prior fluid aspiration. The results of these three steps is that, when aspiration of the fluid has been completed, the pressure in the container is substantially equal to the pressure outside the container, so that there is substantially no expansion or contraction of the separator bubbles when the probe is withdrawn.

For a third embodiment of the invention, where the pressure in the container, at least before the probe is inserted, is known, the air volume change in the at least one bubble which would occur when the probe is removed from the container as a result of the difference in the pressure inside and outside the container is initially computed, and a volume of fluid is withdrawn from the probe which is related to at least the sum of the volumes of the selected quantity of fluid to be aspirated, and the at least one air bubble, plus or minus the air volume computed during the prior step. Again, after the probe is inserted in the container, a volume of air is dispensed from the probe into the container which is substantially equal to the volume of fluid previously withdrawn from the probe less, the volume of at least one of the air bubbles. a single probe may be utilized to withdraw samples from a plurality of different containers before dispensing the contents of the probe, the at least one step performed at selected stages in the method to assure that the sample extends to and only to the end of the probe may be performed for each sample aspirated.

The foregoing and other objects, features and advantages of the invention will be apparent from the following more particular description of preferred embodiments of the invention as illustrated in the accompanying drawings.

IN THE DRAWINGS

DETAILED DESCRIPTION

Figure 1:
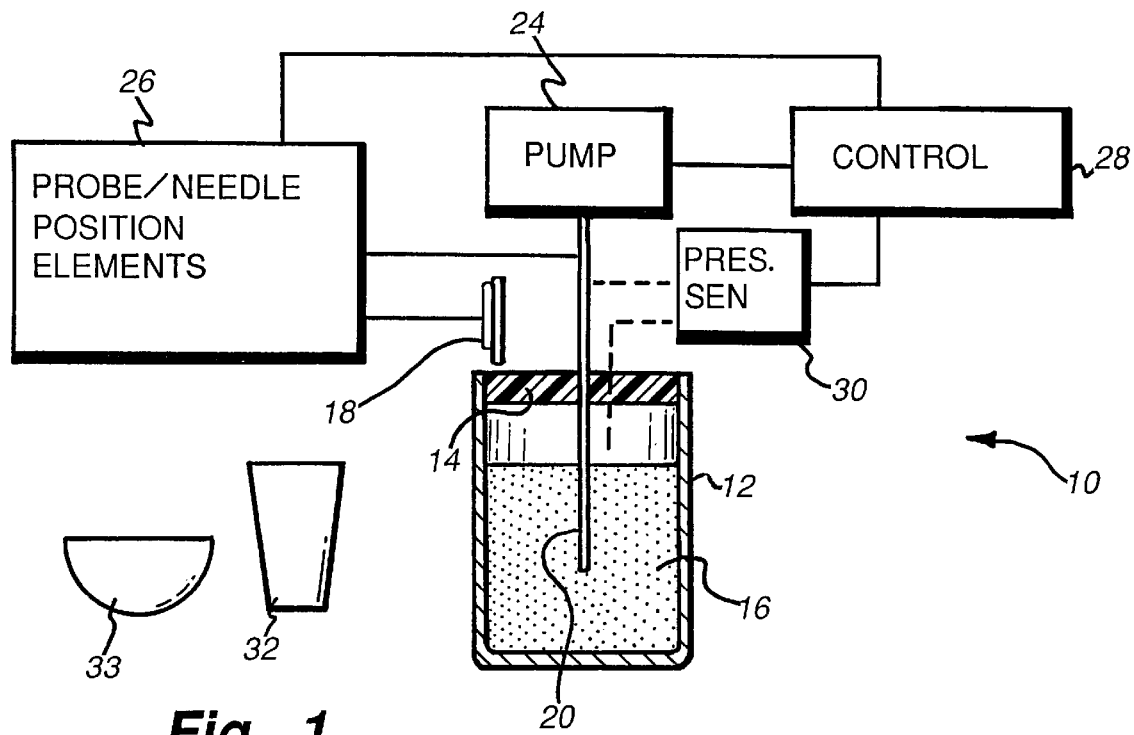
FIG. 1 is a semiblock diagram of a fluid aspirating and dispensing system in which the teachings of this invention might be employed.

FIG. 1 illustrates a fluid aspirating and dispensing system in which the teachings of this invention might be employed. Referring to FIG. 1, the system 10 includes a jar, test tube or other container 12 which is sealed by a seal 14 of a type known in the art which may be pierced a number of times by a needle or probe and will reseal after each piercing. Such seals are typically formed of a plug or membrane of a rubber or other elastomeric material. Container 12 may be filled to a selected level with a fluid 16 to be aspirated. The fluid 16 may for example be blood or some other bodily fluid on which various medical tests are to be performed or may be some chemical substance in fluid form which is to be dispensed in relatively small, precise quantities. A hollow needle 18 is provided which may, for at least one embodiment of the invention, be used to prepierce seal 14 to equalize the pressure inside and outside of the container and a probe 20 is provided which is used for aspirating the fluid. The aspiration of fluid 16 into probe 20 and the dispensing of fluid from the probe is caused by a pump 24 while both the horizontal and vertical positions of the probe are controlled by probe/needle positioning elements 26. As its name suggests, elements 26 also control at least the vertical position of needle 14. Positioning elements 26 may be any of a variety of devices known in the art for performing such mechanical positioning including mechanical positioners using for example electric motors, gears, cams and the like, pneumatic or hydraulic positioners, electromagnetic positioners, etc. The operation of the pump 24 and of positioning elements 26 are controlled by electrical controls 28 which may, for example, include a programmed general purpose computer. For most application, a microprocessor would be adequate for implementing the functions of control 28; however, the controls for implementing this invention may also be performed as one of the functions for a larger general purpose processor which is also used for controlling other operations, special purpose controls may be used in control circuit 28, or the functions of this circuit may be performed by some combination of hardware and software. One input to control 28 for an embodiment of the invention is the output from pressure sensor(s) 30. Pressure sensor(s) 30 may receive its input from a selected point on probe 20 (or on the tubing leading from the probe to the pump) or some type of pressure transducer may be mounted in container 12 with the output from this transducer being passed through seal 14 or otherwise being outputted from the container. Finally, FIG. 1 shows a cuvette or other vessel 32 in which the fluid collected or aspirated into probe 20 may be dispensed for subsequent use and a waste fluid receptacle 33.

Figure 2A:
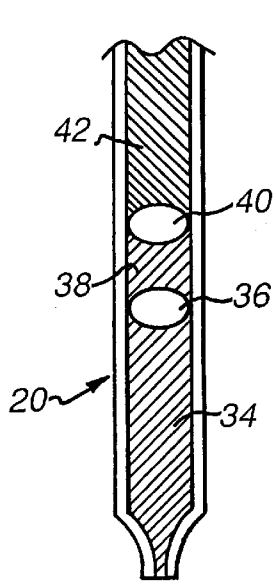
FIG. 2A is a diagram illustrating a probe having fluid aspirated therein, with the fluid sample at the desired position at the end of the probe.

Referring to FIG. 2A, the lower portion of a probe 20 is shown, which portion contains, starting from the tip of the probe, the sample 34, at least a portion of which is to be dispensed into vessel 32, a separator air bubble 36, a separator sample 38, a second separator air bubble 49, and a fluid 42, which may for example be water or some other inexpensive fluid, which extends between separator bubble 40 and pump 24, and is the fluid operated on by the pump to aspirate or dispense a sample from the probe. Separator bubbles 36 and 40 may in fact be one or more bubbles and, in conjunction with separator sample 38, are utilized to prevent any leakage or contamination of the sample 34 from the operating fluid 42.

When performing a dispensing operation, pump 24 is operated in a manner known in the art to pass a precise quantity of the operating fluid 42 into the probe, causing a similar precise quantity or volume of the sample to be dispensed. So long as the fluid sample 34 is initially and finally flush with the tip of the probe as shown in FIG. 2A, the amount of fluid dispensed will in fact be equal to the precise quantity of fluid which is passed by the pump. However, as discussed earlier, if the pressure in the container 12 is less than the pressure outside the container, which is generally the case for reasons to be discussed shortly, then when the probe 20 is removed from container 12, separator air bubbles 36 and 40 will be subjected to a higher external pressure than their internal pressure, and therefore will contract slightly until an equilibrium is established. This contraction of bubbles 36 and 40 can result in the sample 34 moving away from the tip of the probe as shown in FIG. 2 B. This space or gap 44 causes a slight shortfall in the amount of fluid dispensed since the initial operation of the pump moves the sample down to fill the gap 44 rather than dispensing fluid. Similarly, if the pressure in container 12 is greater than the pressure outside the container, when the probe is removed from the container, pressure inside bubbles 36 and 40 will be greater than the outside pressure, causing the bubbles to expand slightly. This can result in a droplet 46 being formed at the end of the probe which can be dispensed with the measured sample, causing the amount of fluid dispensed to be slightly greater than the amount to be provided. A primary objective of this invention is to assure that a gap 44 or a droplet 46 does not exist at the end of the probe before fluid sample 34 is being dispensed from the probe into a utilization vessel such as cuvette 32.

Figure 3:
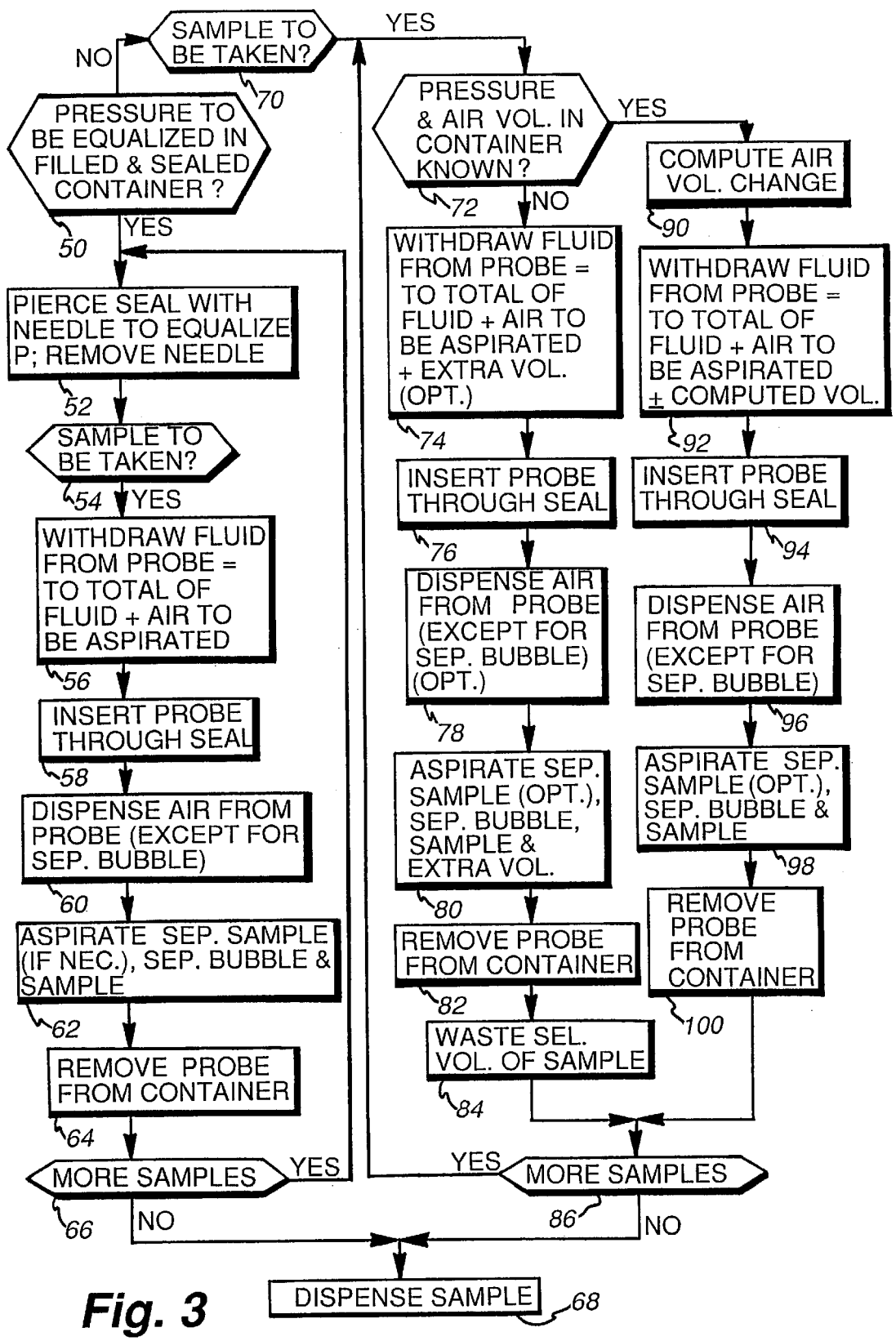
FIG. 3 is a flow diagram illustrating the operations for the various embodiments of the invention.

FIG. 3 is a flow diagram which illustrates three embodiments for practicing the teachings of this invention. While the diagram provides the option for practicing all three embodiments, in a typical implementation, only one of the three embodiments would normally be employed. Further, one of the embodiments is shown as having two possible implementations, although only a single one of such implementations would typically be employed in a given application.

With the above in mind, the first step in FIG. 3 is a determination as to whether pressure is to be equalized in the filled and sealed container 12 before an aspiration operation is performed. This step, step 50, would, however, not typically be performed by controller 28, but would instead be a decision made by the system designer. Assuming a "yes" output during step 50, operations are performed in accordance with a first embodiment of the invention. For this embodiment, the first step, step 52, is to pierce seal 14 with hollow needle 18. This operation is performed by having control 28 operate position elements 26 to forcefully lower needle 18 against seal 14 to cause the needle to puncture and pass through the seal. Needle 18 only pierces the seal sufficiently so as to enter the air space in container 12 above fluid 16, and does not penetrate deeply enough so as to enter the fluid. Thus, air may flow through needle 18 in a proper direction to equalize the pressure between the inside and outside of the container, the needle remaining in the container long enough for this equalization to occur. When a sufficient period of time has passed for pressure equalization to occur, elements 26 are operated to raise needle 18 to remove it from the container, seal 14 reclosing on the removal of the needle to reseal the container. The exact mechanism for moving needle 18 vertically, and if necessary horizontally, does not form part of the present invention and various mechanical, hydraulic, electromagnetic, pneumatic or other techniques known in the art for effecting such mechanical movements may be utilized. As will be discussed in greater detail later, needle 18 may be stationary, and step 52 may be performed by forcefully raising cup 12. During step 52, needle 18 may also be utilized to aspirate any fluid which has adhered to seal or stopper 14. Such fluid may contaminate a sample and this operation permits its presence to be detected.

Once step 52 has been completed, the operation proceeds to step 54 to determine if a sample is to be taken. If for example a determination is made that the sample is contaminated, a "no" output might be obtained during step 54 causing the aspiration to be aborted. Otherwise, when control 28 determines that a sample is to be taken, a "yes" output is obtained from step 54, causing the operation to proceed to step 56 during which pump 24 is operated to withdraw fluid from the probe 20. The total volume of fluid withdrawn during step 56 is substantially equal to the sum of the volumes for sample 34, air bubble(s) 36, separator sample 38, and air bubble(s) 40. When fluid is withdrawn from probe 20 by pump 24, a volume of air equal to the volume of fluid removed is sucked into the probe.

When step 56 has been completed, the operation proceeds to step 58 to insert probe 20 through seal 14. Again, this operation is performed by position elements 26 under control of controls 28 in manners known in the art which do not form part of the present invention. Once probe 20 has pierced seal 14, and either before or after probe 20 has entered fluid 16, but preferably before entering the fluid, pump 24 is operated to perform step 60. During step 60, substantially all the air that was sucked into the probe during step 56 is pushed from or dispensed from the probe except for the separator bubble(s) 40 which remains in the probe below fluid 42.

Once step 60 has been completed, pump 24 is operated to aspirate the separator sample 28, assuming this sample is used. The probe is then removed from fluid 16 and air bubble(s) 36 is aspirated into the probe before the probe is reinserted in the fluid and the sample 34 is aspirated. The volume of sample 34 will be at least equal to the volume of the one or more samples of the fluid which are to be subsequently dispensed and is preferably slightly greater than the total volume of fluid to be dispensed. The aspirating of fluid and air bubbles is performed during step 62. Once the aspirating operation 62 is completed, the operation proceeds to step 64 to remove the probe from the container.

Figure 2B:
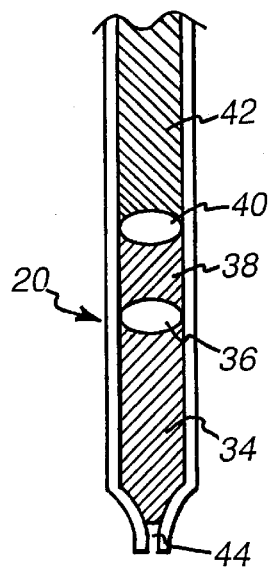
FIG. 2B is a diagram of the same probe where, because of the pressure inside the container being less than that outside, separator air bubbles have contracted upon withdrawing the probe from the container, causing the sample to recede from the tip.
Figure 2C:
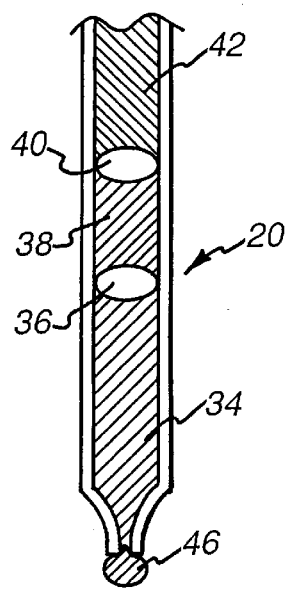
FIG. 2C is a diagram of a probe of the type shown in FIG. 2A illustrating the formation of a drop extending from the tip of the probe when the separator air bubbles expand as a result of the pressure in the container being greater than that outside.

The effects of the operation as described above are that the pressure in the container 12 is initially equalized to the pressure outside the container. Then, during step 60, the container is pressurized by an amount which is substantially equal to the pressure drop in the container which will occur as a result of the aspiration of the fluid and air bubbles therefrom. Thus, at the end of step 62, the pressure in the container is again substantially equal to the pressure outside the container, so that when, during step 64, the probe is removed from the sealed container, the pressure in the bubbles 36 and 40 is substantially equal to the external pressure and no expansion or contraction of these bubbles occurs. The fluid sample 34 therefore extends substantially to the tip of the probe as shown in FIG. 2A rather than being either slightly above or below the tip of the probe as shown in FIGS. 2B and 2C, respectively.

Once step 64 has been completed, the operation may proceed to step 66 to determine if more samples are to be taken from closed containers for the given probe. It is noted that the sample 34 taken from a single container 12 may be sufficient for dispensing into several vessels 32. The determination during step 66 is whether samples of a dilutant, catalyst, or other fluid are also to be aspirated into the probe 20 from closed containers before fluid is dispensed into vessel 32. Assuming a "yes" output is obtained during step 66, the operation returns to step 52 (preferably through a standard probe wash step which is not shown) to equalize the pressure in the container 12 for this new sample, and then through steps 54–66 to take the new sample. It is noted that at least one air bubble will be provided to separate the new sample from the old sample, this being done primarily to prevent leaking of the sample 34 previously taken into the fluid 16 in the new container. It is also noted that the greater the number of air bubbles in the pipette when the dispensing of samples finally occurs, the greater the potential for error and therefore the more important the teachings of this invention become. Finally, it should be noted that while in FIG. 3 it is assumed that the same embodiment of the invention is being practiced for all of the samples during a given loading of a pipette, this is also not a limitation on the invention and a "yes" output from step 66 could lead back to step 50 rather than to step 52. However, the most likely mode of operation would be that shown.

Either from step 64 if the system is designed to operate with only a single sample for each operation, or from step 66 when this step is utilized and a "no" output is obtained during this step, the operation proceeds to step 68 to cause the sample to be dispensed into vessel 32. Again, all of the sample may be dispensed into a single vessel 32, or step 68 may involve a sequence of dispensing operations into a number of cuvettes or other vessels 32. For these operations, position elements 26 may be operated to move the probe 20 in a horizontal or lateral direction to be successively positioned over the vessels 32 or the probe may be laterally moved to a dispensing station, with the vessels 32 being successively moved under the probe to have the fluid samples dispensed therein. Dispensing is accomplished in standard fashion by operation of pump 24.

If during step 50 a determination is made that pressure is not to be equalized, the operation proceeds to step 70 to determine if a sample is to be taken. If a sample is to be taken, the operation proceeds to step 72 to determine if the pressure and air volume in the container is known or unknown. Again, step 50 would probably be performed by the system designer and not by control 28, and the same would probably also be true of step 72. Thus, assuming the system was not to operate in an equalization mode resulting from the use of a piercing needle 18, and that a pressure sensor 30 was not provided, the first step in the operation, once it was determined that a sample was to be taken, would be step 74. This step is similar to step 56 with the pump being operated prior to the probe being inserted in the container to remove a quantity of fluid substantially equal to that of the fluid and air to be aspirated, except that for step 74 a selected extra volume of fluid is also withdrawn during this step, which volume is greater than the maximum volume of the gap 44 which could result from shrinkage of air bubbles in the probe such as the air bubbles 36 and 40. For reasons which will be discussed later, step 74 is optional for this embodiment of the invention and may not in fact be performed for the most preferred embodiment of the invention. Either after step 74 has been completed, or after a decision is made that a sample is to be taken if step 74 is not to be performed, the operation proceeds to step 76 to insert the probe through seal 14 in the same manner as for step 58, and to step 78 to dispense substantially all the air which was sucked into the probe during step 74 into the container in the same manner as for step 60. Step 78, like step 74, is optional for this embodiment of the invention, and step 78 would be performed only if step 74 is also performed. If steps 74 and 78 are not performed, then either before or after step 76 is performed, and preferably after step 76, a sufficient quantity of fluid would be withdrawn from the probe, with the probe out of the fluid to create the air bubble(s) 40.

Once these operations have been completed, sample and additional air bubbles would be aspirated during step 80 and an extra volume would also be aspirated during this step, which volume is, as previously indicated, somewhat greater than the maximum volume which could occur for gap 44 as a result of bubble shrinkage. When aspiration has been completed, the probe is removed from container 12 during step 82 and the operation then proceeds to step 84 during which a selected volume of the sample is wasted. In particular, since the initial pressure in the container is not equalized and is not know, the most that can be accomplished by steps 74 and 78 is to make sure that the pressure change resulting from the removal of fluid and air from the container does not aggravate the pressure imbalance so that the pressure imbalance between the inside and outside of the container when aspiration of fluid has been completed (i.e. after step 80) is the same as the pressure balance was when the probe was originally inserted. If the pressure in the container 12 is less than the external pressure, this operation will in fact be advantageous since it will result in there being a smaller pressure differential when the probe is removed, and thus less shrinkage to be compensated for. However, if the pressure in the container was initially greater than the external pressure, these operations will aggravate rather than alleviate the problem. Since initial vacuum pressure is frequently employed in the containers, since removal of fluid and air from the containers normally results in a reduction of pressure in the container and since the temperature of the blood in the container under ambient conditions is generally less than that of the blood when it was initially loaded into the container, resulting in a slight decrease in the volume of the fluid which reduces pressure, it is significantly more probable that the pressure in the container 12 is less than the external pressure than that it is greater. However, there are also circumstances under which the pressure may be greater, and steps 74 and 78 would not be employed in such environments. Further, since steps 74 and 78 cannot assure that there will be no gap 44 or bubble 46, this being prevented by the initial pressure in the container being unknown, additional compensation step 84 is required in any event. Therefore, the only advantage in performing steps 74 and 76 is that they generally will result in less sample being wasted during step 84. Except in cases where the sample fluid is particularly valuable or in particularly short supply, this advantage may not justify the additional time and processing effort involved in performing steps 74 and 76. In any event, during step 84, the amount of fluid wasted would be an amount substantially equal to or greater than the maximum anticipated gap 44 which could occur, but less than the extra volume aspirated during step 80. This extra volume would be dispensed by pump 24 into a suitable receptacle 33 for disposal. Therefore, when step 84 has been completed, to the extent there was a gap 44, it no longer exists. Further, to the extent there was a droplet 46, it has also been dispensed and no longer exists. Therefore, at the end of step 84, the probe is in the desired state shown in FIG. 2A.

From step 84, the operation proceeds to step 86 to determine if more sample are to be taken, step 86, like step 66, being optional. If a "yes " output is obtained during step 86, the operation may return, preferably through a wash step (not shown), to step 72 (as shown), or may return to step 50, step 70 or step 74, the step returned to depending on the options which the system designer wishes to provide. When, from step 84 or 86, a determination is made that there are no more samples to be taken, the operation proceeds to step 68 to cause the samples to be dispensed in the manner previously indicated.

If during step 72 a "yes" output is obtained, meaning that there is a pressure-sensing device 30 for example, and that the air volume in the container is known or has been determined utilizing one of a number of known techniques, the detected pressure and air volume are utilized during step 90 to determine the exact change in air bubble volume which will occur as a result thereof. It is noted that the pressure differential may be either plus or minus so that the change in air volume may also be either an increase in air volume or a decrease.

During step 92, the next step in the operation, pump 24 is operated to remove a volume of fluid from the probe which, as for steps 56 and 74, is substantially equal to the volume of the areas 34, 36, 38 and 40, except that during step 92 this volume is either increased or decreased by an amount which is related to the volume computed during step 90. From step 92, the operation proceeds to step 94 to insert the probe through the seal and step 96 to dispense the air which has been sucked into the probe back into container 12 except for the air bubble(s) 40. Step 98 is then performed which causes the sample 34, air bubble(s) 36 and sample 38 to be aspirated. The effect of steps 92, 96 and 98 is that, at the end of step 98, the pressure in container 12 is substantially equal to the external pressure so that, when the probe is removed from the container during step 100, there is substantially no expansion or contraction of the separator air bubbles. Thus, there is substantially no air gap 44 or overshoot droplet 46. From step 100, the operation returns to step 86, if this operation is to be performed, to determine if more samples are to be taken. When more samples are not to be taken, the operation proceeds to step 68 to cause the sample or samples to be dispensed in the manner previously indicated.

Each of the embodiments discussed above has certain advantages and disadvantages so that the embodiment which is preferred will vary with application. Since the second embodiment, without steps 74 and 78, is the simplest embodiment, this embodiment might be preferred where wasting of a certain amount of the sample fluid 16 is not a problem. If the loss of sample is a problem, then the third embodiment may be preferred where speed is a factor since the extra electrical operations for this embodiment will take less time than the mechanical operation of step 52 in equalizing pressure. However, the requirement to take accurate pressure and volume readings for this embodiment of the invention and the extra processing steps involved in performing calculations are possible disadvantages for this embodiment. The accuracy of results using this embodiment will also depend on the accuracy with which pressure readings and volume determinations can be quickly taken and the accuracy of the computations. In addition to the possible time loss from mechanical operations, the first embodiment may also be a potential problem, particularly if the pressure in the container is greater rather than less than the external pressure, in that some blood may squirt out through the needle when the needle is inserted. A trap may be provided to deal with this problem.

While an exemplary embodiment has been shown in FIG. 1, it is apparent that this is only for purposes of illustration and that the invention can be implemented on a wide variety of available equipment or on equipment to be developed in the future. Controls may be of a variety of types as previously indicated. In particular, while in FIG. 1 it is assumed that the container 12, vessel 32 and waste fluid receptacle 33 are stationary and that position elements 26 move needle 18 and probe 20 to perform the various puncturing, aspirating and dispensing operations, this is not a limitation on the invention and the invention could just as easily be practiced with needle 18 and/or probe 20 being stationary and container 12 being moved laterally by suitable equipment known in the art to position it under the needle and probe and/or being raised and lowered to facilitate piercing of seal 14 by needle 18 and/or probe 20 and removal of the needle and/or probe from the container. Vessel 32 and/or waste fluid receptacle 33 could be similarly moved relative to the probe. Thus, while the invention has been particularly shown and described above with reference to preferred embodiments, the foregoing and other changes in form and detail may be made therein by one skilled in the art without departing from the spirit and scope of the invention.

What is claimed is:

1. A method for aspirating a fluid from a sealed container and for dispensing a precise quantity of the fluid comprising the steps of:

(a) inserting a probe into the container through a seal formed thereon while maintaining the container sealed;

(b) providing at least one air bubble in the probe to separate any sample from other fluid in the probe;

(c) aspirating a selected quantity of the fluid into the probe;

(d) removing the probe from the container;

(e) dispensing a precise quantity of the fluid from the probe; and (f) performing at least one step at selected stages in the method to assure that, before step (e) is performed, any expansion or contraction of the at least one air bubble in the probe as a result of any pressure differential between the inside and outside of the sealed container is compensated for so that sample fluid in the probe extends to the end of the probe without any of the fluid extending beyond the end of the probe.

2. A method as claimed in claim 1 wherein step (c) includes the step of aspirating both the selected quantity of fluid to be aspirated and a selected extra volume of fluid, and wherein step (f) includes the step performed between steps (d) and (e) of (g) wasting a selected quantity of the sample which is greater than the maximum amount the at least one air bubble might shrink as a result of the pressure in the container being less than the pressure outside the container, but less than said selected extra volume of fluid.

3. A method as claimed in claim 2 wherein the pressure in the container both before step (a) is performed and after step (c) is performed are unknown, and at least one of these pressures differs from the pressure outside the container; and including the steps performed before and after step (a), respectively, of:

(h) withdrawing a volume of fluid from the probe which is substantially equal to at least the sum of the volumes of the selected quantity of fluid to be aspirated, the at least one air bubble and the selected extra volume of fluid, a volume of air entering the probe to replace the volume of fluid; and (i) dispensing a volume of air from the probe into the container which is substantially equal to the volume of fluid withdrawn during step (h) less the volume of at least one of said air bubbles.

4. A method as claimed in claim 1 wherein step (f) includes the steps performed before step (a) of:

(j) equalizing the pressure inside and outside the container;

(k) withdrawing a volume of fluid from the probe which is equal to at least the sum of the volumes of the selected quantity of fluid to be aspirated and the at least one air bubble, a volume of air entering the probe to replace the volume of fluid; and the step performed after step (a) of (l) dispensing a volume of air from the probe into the container which is substantially equal to the volume of fluid withdrawn during step (k) less the volume of at least one of said air bubbles.

5. A method as claimed in claim 4 wherein step (j) includes the step of inserting a hollow needle through the container seal and removing the needle before step (a) is performed.

6. A method as claimed in claim 1 wherein the pressure in said container before step (a) is performed is known, and step (f) includes the steps performed before step (a) of:

(m) computing the air volume change in the at least one bubble which would occur after step (d) as a result of the difference between the pressure inside and outside the container;

(n) withdrawing a volume of fluid from the probe which is substantially equal to at least the sum of the volumes of the selected quantity of fluid to be aspirated, the at least one air bubble, the air volume computed during step (m); and the step performed after step (a) of (o) dispensing a volume of air from the probe into the container which is substantially equal to the volume of fluid withdrawn during step (n) less the volume of at least one of said air bubbles.

7. A method as claimed in claim 1 wherein steps (a)–(d) may be performed a plurality of times with a given probe for different containers and samples before step (e) is performed, and wherein step (f) is performed for each iteration of steps (a)–(d).

8. A method for aspirating a fluid from a sealed container and for dispensing a precise quantity of the fluid comprising the steps of:

(a) inserting a probe into the container through a seal formed thereon while maintaining the container sealed;

(b) providing at least one air bubble in the probe to separate any sample from other fluid in the probe;

(c) aspirating a selected quantity of the fluid into the probe, said selected quantity including at least a volume of fluid to be dispensed and a selected extra volume of fluid;

(d) removing the probe from the container;

(e) wasting a selected quantity of the sample which is greater than the maximum amount the at least one air bubble might shrink as a result of the pressure in the container being less than the pressure outside the container, but less than said selected extra volume of fluid; and (f) dispensing the precise quantity of fluid to be dispensed from the probe.

9. A method as claimed in claim 8 wherein the pressure in the container both before step (a) is performed and after step (c) is performed are unknown, and at least one of these pressures differs from the pressure outside the container; and including the steps performed before and after step (a), respectively of:

(g) withdrawing a volume of fluid from the probe which is substantially equal to at least the sum of the volumes of the selected quantity of fluid to be aspirated, the at least one air bubble and the selected extra volume of fluid, a volume of air entering the probe to replace the volume of fluid; and (h) dispensing a volume of air from the probe into the container which is substantially equal to the volume of fluid withdrawn during step (g) less the volume of at least one of said air bubbles.

* * * * *